US00PP14438P29

(12) United States Plant Patent
Whitcomb

(10) Patent No.: US PP14,438 P2
(45) Date of Patent: Dec. 30, 2003

(54) CRAPE MYRTLE PLANT NAMED 'WHIT VI'

(50) Latin Name: *Lagerstroemia indica*
Varietal Denomination: Whit VI

(75) Inventor: Carl Whitcomb, Stillwater, OK (US)

(73) Assignee: Lacebark, Inc., Stillwater, OK (US)

( * ) Notice: Subject to any disclaimer, the term of this patent is extended or adjusted under 35 U.S.C. 154(b) by 0 days.

(21) Appl. No.: 10/189,786

(22) Filed: Jul. 3, 2002

(51) Int. Cl.[7] ..... A01H 5/00
(52) U.S. Cl. ..... Plt./252

(58) Field of Search ..... Plt./252

*Primary Examiner*—Kent Bell
(74) *Attorney, Agent, or Firm*—Streets & Steele; Jeffrey L. Streets; Frank J. Campigotto

(57) ABSTRACT

A new and distinct variety of crape myrtle, *Lagerstroemia indica*, which is characterized by a dense, upright growth habit; leathery leaves which emerge crimson and change to dark green; low seed production (plant is semi-sterile); inflorescences which are 4 to 14 inches tall and 4 to 12 inches wide; flower buds which are green to crimson; and flowers which are white with transition to light crimson. The new variety is also characterized by a long bloom period.

4 Drawing Sheets

Genus, species: *Lagerstroemia indica*.
Variety denomination: crape myrtle WHIT VI.

BACKGROUND OF THE INVENTION

The present invention relates to a new and distinct variety or cultivar of the ornamental shrub, *Lagerstroemia indica*, commonly known as crape myrtle.

The crape myrtle shrub is native to eastern China and was introduced into North America in the late 1700's. Since then, this popular ornamental shrub has been grown extensively across the southern half of the continent. Over the years, seedlings of *Lagerstroemia indica* or hybrids between *L. indica* and *L. fauriei* have been selected for various growth forms, flower colors, or other features and propagated asexually. An assortment of methods has been utilized in attempting to develop improved varieties of crape myrtle and several have had U.S. Plant Patents issued.

For example, U.S. Plant Pat. No. 4,182, U.S. Plant Pat. No. 4,183, U.S. Plant Pat. No. 4,184 and U.S. Plant Pat. No. 4,185 disclose and claim a series of four new varieties of *Lagerstroemia indica* produced by crossing previously known varieties. Each of these varieties was characterized as having a weeping growth habit at maturity. U.S. Plant Pat. No. 5,302, also discloses a new variety of crape myrtle exhibiting a weeping growth habit at maturity.

U.S. Plant Pat. No. 6,365 and 6,383 disclose varieties of crape myrtle derived from seedlings treated with a mutation-inducing chemical. U.S. Plant Pat. Nos. 10,296 and 10,297 and 10,319 and 11,312 and 11,342 also disclose new varieties of crape myrtle derived from seedlings where one or more of the parents were treated with a mutation-inducing chemical.

It is generally known that ethyl methane sulfonate (EMS), sodium azide, and colchicine are capable of producing plant mutations. Since one or more of the grandparents of the new variety of crape myrtle were treated with these compounds, the present invention may be such a mutant.

SUMMARY OF THE INVENTION

The present invention involves the discovery of a new and distinct variety of crape myrtle, *Lagerstroemia indica*, which has been given the cultivar name 'Whit VI' and is characterized by a vigorous, broad, upright growing, large shrub or small tree with moderate branching that may reach a height of 10 to 15 feet at maturity. Leaves of the plant emerge crimson and slowly change to dark green with age with mid-veins and backs retaining some crimson color when leaves are in full sun. Mature leaves are larger and more leathery than is typical of the species. Twigs of current season's growth are distinctly crimson unless shaded by other leaves or branches. Inflorescences are 4 to 14 inches tall and 4 to 12 inches wide. Flower buds are green when shaded but light crimson on any parts exposed to full sun, with the margins of the bud scales crimson. Individual petals are pure white, except at the base, which is distinctly, light crimson. Flowers that open during very cool weather in late fall are slightly pinkish throughout. Stamens are prominent and bright yellow. Old flowers fall from the inflorescence with little discoloration. Flowering generally begins in July in North Central Oklahoma and flowering continues until frost. Seed head production is light during July and August and heavier during September and October.

DETAILED BOTANICAL DESCRIPTION

Figure 1:
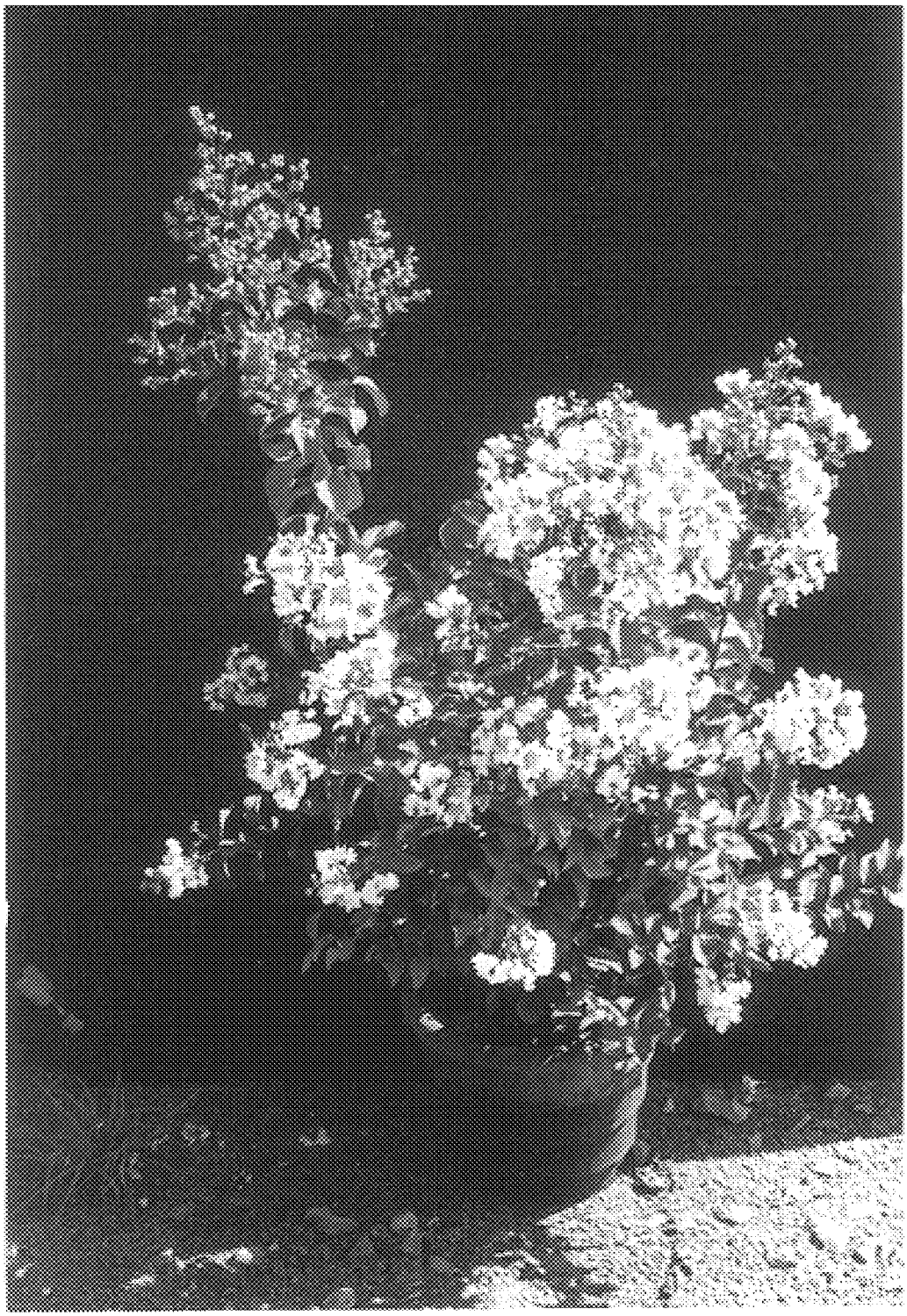
FIG. 1 is a photographic view in full color of the growth and flowing of my new crapemyrtle plant in a 3-gallon container.

The new variety of crape myrtle, which has been given the cultivar name 'Whit VI', was selected from about 2,600 seedlings grown from a $7^{th}$ generation original seedling plant from when this research began in 1986. The parent seedling selected because of the upright growth, exceptional vigor and prolific lavender flowers that produced many seed pods and viable seeds. The female parent plant grew from seeds that had been treated with a combination of EMS, sodium azide, and colchicine. No attempt was made to control pollination; therefore the pollen could have come from any of the surrounding crape myrtle seedlings that had also been treated. Seeds were planted in flats. After the seeds germinated, seedlings were transplanted into small containers and mildew was introduced. Seedlings susceptible to mildew or with poor vigor were rouged out. The remainder of the seedlings were planted in rows in an open field for further evaluation.

The new variety was one of 31 seedlings from the population of approx. 2,600 seedlings from this original seedling plant that produced white flowers. The new variety was selected for the crimson new foliage, profusion of flowers in panicles that appear pure white from a distance, dense, upright growth, leathery foliage, and resistance to powdery mildew and resilience following early fall freezes. It may be a mutant seedling arising from the chemical treatment of the female parent seedling.

Softwood cuttings taken from the original Whit VI plant have been successfully rooted in a medium of peat and perlite under intermittent mist. Subsequent cuttings from plants produced from the previous cuttings of the WHIT VI original plant have been similarly rooted. Growth, flowering, and flower and foliage color remain consistent with the parent. The plant does produce seeds but viability is low and seedlings are unlike WHIT VI. Asexual reproduction of the new plant by cuttings taken in Stillwater, Okla., has shown that the unique features of this new crape myrtle are stable and reproduced true to type in successive generations.

A detailed description of the new variety of crape myrtle follows: Unless otherwise noted, the description is of a container grown plant, approximately one years old, grown in a three gallon container in north central Oklahoma.

Parentage: Selected from over 150,000 crape myrtle seedlings grown from a selected seedling parent through seven generations. Seed resulting in the immediate female plant had been treated with a combination of EMS, sodium azide, and colchicine known to induce mutations. The male parent is not specifically known as pollination resulted from natural insect activity among hundreds of seedlings adjacent to the female plant. The new variety was one of 31 seedlings from among the population of approximately 2,600 seedlings that produced white flowers. The thick, leathery leaves and partial sterility are suggestions that this may be a mutant seedling.

Growth: The plant is a vigorous, bushy, upright grower when young. The selected plant reached a height of 4.5 feet one year after a cutting was taken from the initially discovered WHIT VI. Three year old plants of WHIT VI in the field are nine 9 feet tall. Based on the growth rate of the WHIT VI, it is estimated that the mature height may be 10 to 15 feet. Vegetative growth is rapid in spring and continues until summer when flowering begins. Only modest growth occurs after the onset of flowering. Unlike most crape myrtle varieties, which produce many vertical stems creating a dense shrub, this new crape myrtle typically produces 3 to 5 vertical stems with moderate side branches, creating a dense but upright form.

Branches: Current season's stems, exposed to direct light are crimson, greyed-purple group 187-A and CIE .410, .298, 3.4 (color notations from The Royal Horticulture Society Colour Chart, 1966 and the Comission International de l'Eclairage, 1931). The length of branches is dependant upon the growing conditions of the plant, ranging from about 3 inches to more than 30 inches long. The diameter of current season's growth ranged from 3/32 inch to about 11/32 inch.

Bark: Bark is typical of *L. indica* species and is exfoliating. The bark color of one, two and three year old stems of WHIT VI range from 177 B (CIE .407, .353, 16.1), 177 C (CIE .416, .351, 20.4) or 177 D (CIE .402, .347, 26.9). Four year old stems that have exfoliated range from 199 A (CIE .409, .402, 14.8) or 199 B (CIE .390, .387, 22.1) when shaded or 197 A (CIE .350, .364, 17.9) or 197 B (CE .346, .360, 22.8) when exposed to sun.

Foliage: Upper and lower surfaces of new leaves in the spring emerge crimson, greyed-purple group 187-A and CIE .410, .298, 3.4 and remain so for several weeks with a gradual transition to green with age and maturity. With leaf maturity and the onset of flowering, upper surfaces of leaves are Green group, 139-A and CIE .292, .400, 6.4. to Green group 139-B and CIE .311, .417, 16.0 with only faint traces of earlier crimson color. Under leaf surface of mature leaves are 147 B (CIE .350, .408, 16.6) or 147 C (CIE .347, .399, 31.0) or 148 A (CIE .354, .418, 15.8). When new growth occurs during summer, leaves are crimson, 187-A and CIE .410, .298, 3.4, only until they reach mature size, which is a much shorter time relative to spring. Upper and lower leaf surface colors are the same as for leaves produced in the spring. When mature leaves are folded or positioned such that a portion of the under leaf surface is exposed to sun, the crimson color persist even with age. Foliage color varies with light intensity and growing conditions. Foliage has been very resistant to powdery mildew. Mature leaves are thick and leathery and larger than the species average. Leaf size varies from about 1.0 to about 2.75 inches long by about 0.5 to about 1.5 inches wide, with the widest point approximately at the center. Leaf shapes range from obtuse, acute to slightly acuminate at the tip and obtuse to slightly acute at the base. Petiole is typically absent or very short and not distinct.

Figure 2:
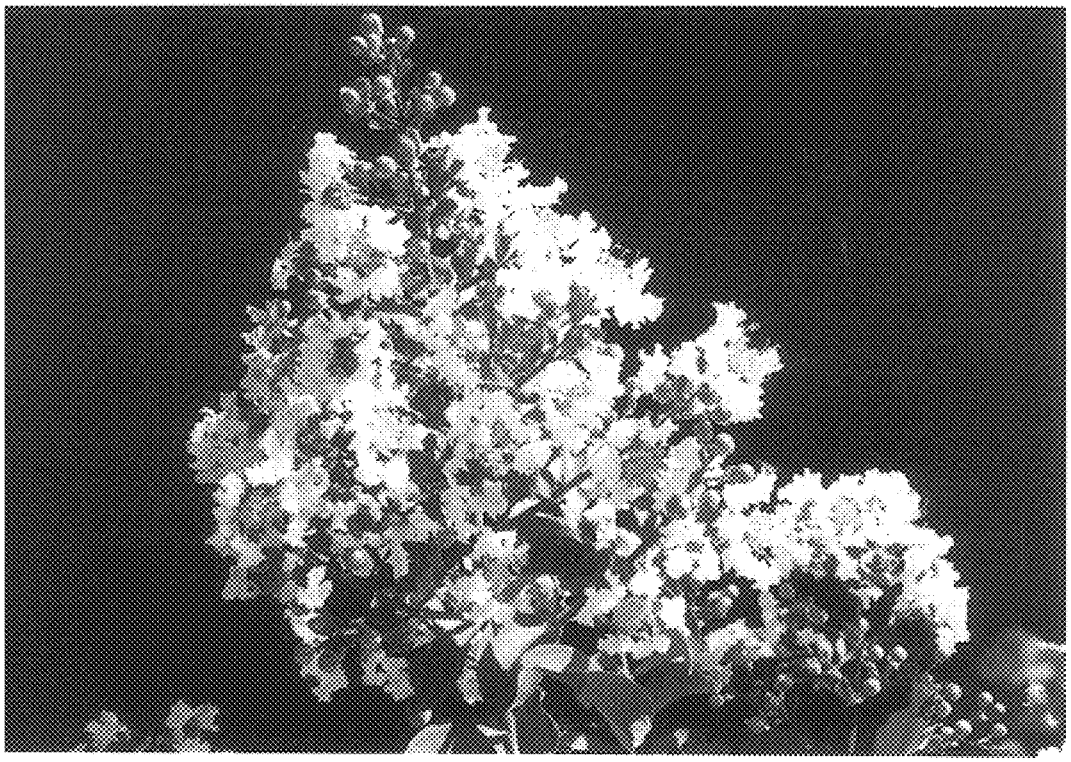
FIG. 2 is a photographic view in full color of white flowers with yellow stamens and variable green flower buds with crimson lines along the margins of the bud scales of the plant in FIG. 1.
Figure 3:
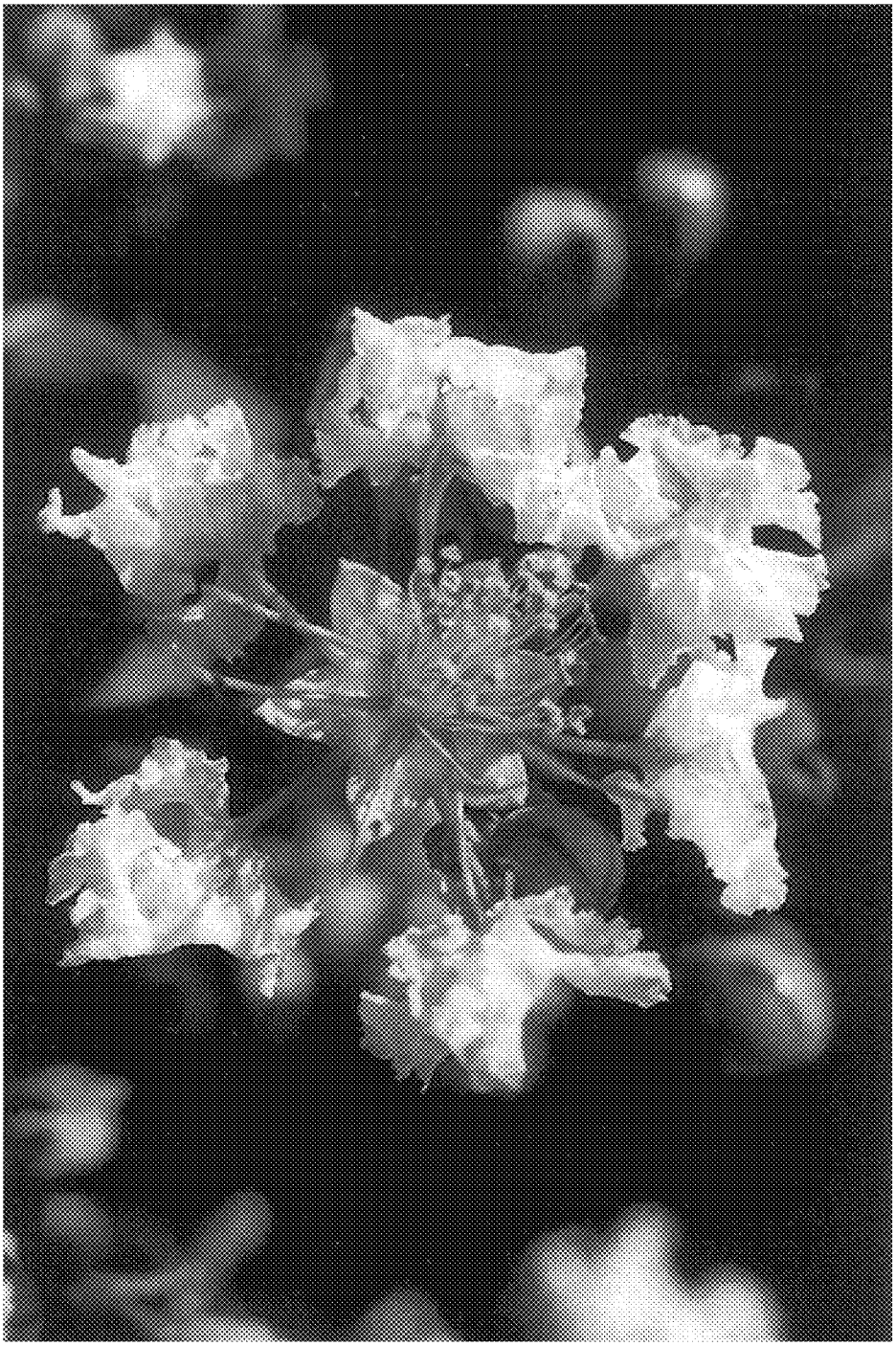
FIG. 3 is a photographic view in full color of an individual flower with white petal blades and light crimson basal portions and yellow stamens, and a green and crimson flower bud showing crimson lines along the margins of the bud scales of the plant in FIG. 1.
Figure 4:
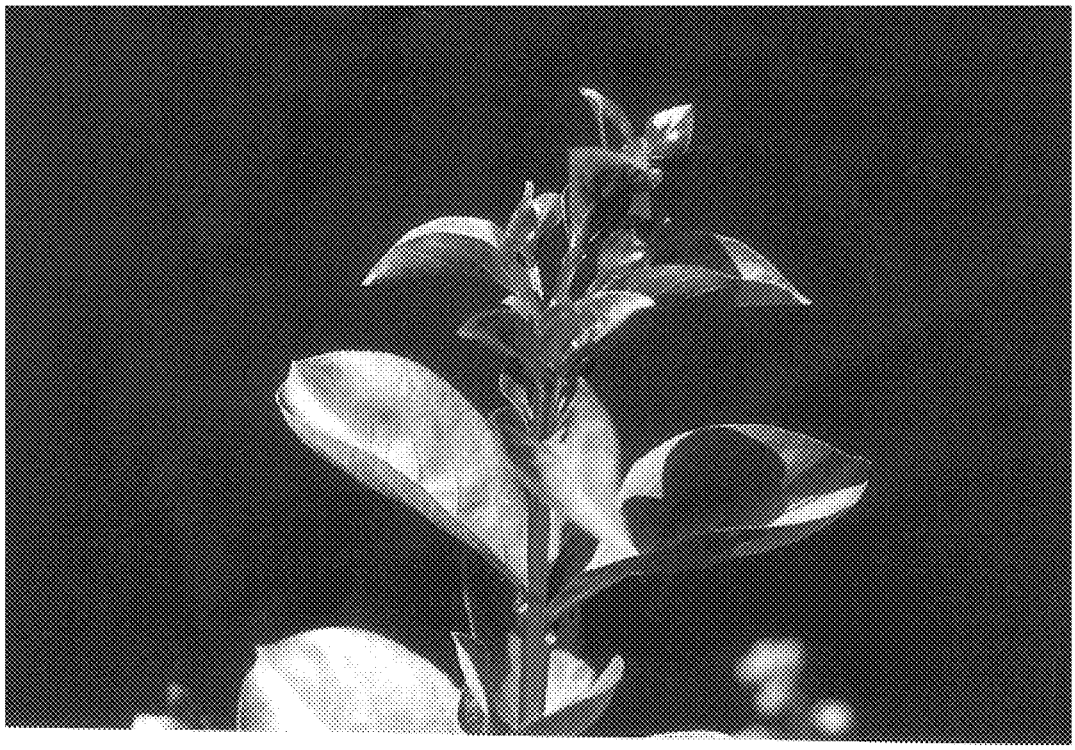
FIG. 4 is a photographic view in full color of crimson new foliage, crimson stems, crimson flower buds and dark green mature foliage of the plant in FIG. 1.

Flowers: Blades of individual petals (expanded apical portion) are white, white group 155-D and CIE .319, .330, 88.6, with transition to light crimson, greyed-purple group 185-C and CIE .417, .293, 16.7, at the claw (the narrowed stalk-like basal portion of the petal) during the summer and early fall. In late fall after temperatures have dropped to near the freezing point and light intensity is low, any late opening flowers are a faint pink, approx. greyed-purple group 186-D and CIE .344, .298, 44.9. The flower petals, typically 6 but occasionally 5, open fully, exposing distinct yellow stamens. (FIGS. 1, 2 and 3). As the flowers age, they typically fall cleanly from the inflorescence without discoloring or becoming unattractive. There are six sepals per bloom, each having the shape of one-sixth of a sphere. Unopened flower buds are round with six distinct lines of dehiscence where they split to reveal the flower. Bud size increases with age to typically 3/16 to 5/16 inch diameter at opening. The unopened flower buds are variable, slight crimson on sides exposed to direct light and mostly light green on shaded sides, with distinct crimson margins of the bud scales, greyed-purple group 187-B and CIE .479, .296, 5.1 (FIG. 3). The diameter of the flower buds varies widely, as does the size of the flower, since the size is so dependant upon the growing conditions. Inflorescences are panicles 4 to 14 inches tall and 4 to 12 inches wide (FIG. 1). The stocks of inflorescences exposed to full sun are crimson, greyed-purple group, 187-A and CIE .410, .298, 3.4. When growing conditions are moderate, with temperatures in the upper 80's to lower 90's and moisture is not limiting, individual flowers remain attractive for as long as 10–15 days. When water is limiting and there are low humidity winds, and growing conditions are not conducive, flowers begin to become unattractive after 4–5 days.

The new variety begins flowering in July and continues into October in North Central Oklahoma. This flowering period is longer than most seedlings and cultivars of crape myrtle known to me. Flowering continues during periods of intense and prolonged heat as long as moisture is available. The plant is semi-sterile which appears to make the blooms last longer than is typical of *L. indica* species. As with other crape myrtle plants, blooms each have six petals per bloom. Bloom diameter varies with environmental conditions. Because the plant is semi-sterile, few viable seeds are produced. The seed pods that form are typical of *L. indica* species.

Cold hardiness: The new variety of crape myrtle has withstood temperatures of 0° F. with no injury. The top of the initially discovered WHIT VI as well as asexually propagated offspring were killed in October 2000 when, on October 3, the temperature was 92° F., then on October 9, dropped to 23° F. With the arrival of spring 2001, all plants produced vigorous growth and were flowering by early July. This was a distinct contrast to many other seedlings under evaluation that were killed entirely or were very slow to recover from the cold injury.

I claim:

1. A new and distinct variety of crape myrtle plant, substantially as illustrated and described.

* * * * *